(12) United States Patent
Silvis et al.

(10) Patent No.: US 8,656,753 B1
(45) Date of Patent: Feb. 25, 2014

(54) SLEEVE UNITS, AND INLET LINER INSERTS THEREFOR, USED FOR PREPARING A SAMPLE FOR GAS CHROMATOGRAPHIC ANALYSIS

(76) Inventors: Paul H. Silvis, Port Matilda, PA (US);
Thomas E. Kane, State College, PA (US)

( * ) Notice: Subject to any disclaimer, the term of this patent is extended or adjusted under 35 U.S.C. 154(b) by 778 days.

(21) Appl. No.: 12/157,202

(22) Filed: Jun. 6, 2008

(51) Int. Cl.
*G01N 30/60* (2006.01)

(52) U.S. Cl.
USPC ............................................ 73/23.41; 95/88

(58) Field of Classification Search
USPC ...................... 73/23.35, 23.41; 95/82, 88, 89
See application file for complete search history.

(56) References Cited

U.S. PATENT DOCUMENTS

| | | | | |
|---|---|---|---|---|
| 2,867,425 | A * | 1/1959 | Teller | 261/95 |
| 3,438,614 | A * | 4/1969 | Lipinski | 261/98 |
| 3,727,451 | A * | 4/1973 | Broerman | 73/23.39 |
| 3,752,453 | A * | 8/1973 | Doyne | 261/94 |
| 3,850,593 | A * | 11/1974 | Beaujean et al. | 62/625 |
| 3,894,943 | A * | 7/1975 | Hartmann et al. | 516/138 |
| 3,902,997 | A * | 9/1975 | Hartmann et al. | 516/137 |
| 4,732,687 | A * | 3/1988 | Muller et al. | 210/656 |
| 5,119,669 | A | 6/1992 | Silvis et al. | |
| 5,194,231 | A * | 3/1993 | Gough et al. | 422/312 |
| 5,660,795 | A | 8/1997 | Schaedlich et al. | |
| 6,301,952 | B1 | 10/2001 | De Zeeuw et al. | |
| 6,448,451 | B1 * | 9/2002 | Rudzinski et al. | 568/682 |
| 6,512,131 | B1 * | 1/2003 | Best et al. | 554/133 |
| 6,572,831 | B1 * | 6/2003 | Nicola | 422/256 |
| 6,779,379 | B2 * | 8/2004 | Grob et al. | 73/23.41 |
| 7,389,678 | B2 * | 6/2008 | Boborodea et al. | 73/61.53 |
| 2002/0020209 | A1 * | 2/2002 | Grob et al. | 73/23.41 |
| 2005/0271545 | A1 * | 12/2005 | Boborodea et al. | 422/68.1 |

OTHER PUBLICATIONS

Mols, Hans G.J. et al., "Large Volume Injection in Capillary GC Using PTV Injectors: Comparison of Inertness of Packing Materials," J. High Resol. Chromatogr., vol. 18, Feb. 1995, pp. 124-128.
SPM Semiconductor Packing Materials' standard wire specifications sheets, entitled, "Standard Gold Wire & Ribbon Products," undated.
De Zeeuw, J. et al., "A Simple Way to Speed up Separations by GC-MS Using Short 0.53 mm Columns and Vacuum Outlet Conditions," J. High Resol. Chromatogr., vol. 23, No. 12, Dec. 2000, pp. 677-680.
Peene, J. et al., "Low Pressure Gas Chromatography: Fast Analysis With High Sensitivity," International Laboratory, Sep. 2000, pp. 41-44.
Restek catalog excerpt found on restek.com. "Splitless Liners for Agilent: 4 mm Splitless," retrieved on Jan. 14, 2008.

(Continued)

*Primary Examiner* — Daniel S Larkin
(74) *Attorney, Agent, or Firm* — McNees Wallace & Nurick LLC (57) ABSTRACT

A sleeve unit for preparing a sample for gas chromatographic analysis comprises an inlet liner having a bore therein, an inlet to the bore, and an outlet from the bore, and an inlet liner insert located with the bore. The inlet liner insert extends across the bore to cause a sample being prepared for gas chromatographic analysis to flow through the inlet liner insert. The inlet liner insert comprises an arrangement of wire, the arrangement creating a restricted pathway for the sample as the sample flows through the bore of the inlet liner to the outlet of the bore, and the wire having a surface having a high thermal conductivity and being substantially chemically inert to the sample.

63 Claims, 6 Drawing Sheets

(56) References Cited

OTHER PUBLICATIONS

Restek catalog excerpt found on restek.com. "Press-Tight Connectors: Deactivated, Universal," retrieved on Jan. 14, 2008.
Stevenson, Robert, "Editor's Page, The World of Separation Science: 22nd International Symposium on Capillary Chromatography." American Laboratory, Aug. 2000, pp. 6-10.
Stevenson, Robert, "Editor's Page, The World of Separation Science: The Smarter the Chromatographer, The Shorter the Columns." American Laboratory, Feb. 2000, pp. 6-10.
Varian Analytical Instruments' brochure, entitled, "Varian Rapid—MS System," undated.
Press Release by Varian, Inc., entitled, "Rapid—MS from Varian, Inc. Boosts GC/MS Productivity up to 10 Fold," undated.
Excerpts from EPA Method 529 (Rev. 1.0), "Illustrating GC—MS Analysis of Explosives without Flow Restriction," undated, www.epa.gov/nerlcwww/m_529.pdf.
Michael A. Goss and Brad Rightnour's presentation at the 2005 Pittsburgh Conference, entitled, "A Comparison of Liner Geometries and Their Effect of Gas Chromatographic Performance," Abstract No. 279-26P, Session 270—Gas Chromatography, Feb. 28, 2005.
Restek catalog, entitled, "Inlet Solutions," 2008.
Restek pamphlet, entitled, "CarboFrit (TM) Inlet Liner Packing," Jun. 2003.

* cited by examiner

SLEEVE UNITS, AND INLET LINER INSERTS THEREFOR, USED FOR PREPARING A SAMPLE FOR GAS CHROMATOGRAPHIC ANALYSIS

BACKGROUND OF THE INVENTION

1. Field of the Invention

This invention relates to gas chromatography (GC) equipment, and more particularly concerns (a) a sleeve unit, which comprises an inlet liner and an inlet liner insert positioned therein, for preparing a sample for gas chromatographic analysis, and (b) the inlet liner insert (packing) itself which preferably comprises an arrangement of gold wire.

2. Background of the Prior Art

In gas chromatography (GC), analysis typically is divided into three stages: (1) sample preparation; (2) separation; and (3) detection. Liquid samples to be tested are vaporized in the sample preparation phase, and conventional gas chromatography (GC) employs liners, most commonly made of glass, as a device where vaporization of the liquid sample takes place. Liners are normally subjected to elevated temperatures, e.g., over 200° C., to enhance the rate of vaporization and reduce sample adsorption on the inner surfaces of the liner. It is common to use packing materials in liners to help promote sample vaporization, trap non-volatile residue, such as solid/high molecular weight contaminants which may be present in "dirty" samples, to prevent column contamination, promote sample vapor mixing to obtain homogenous samples, and assist in reaching an ideal sample vapor residence time in the liner prior to the vapor sample formed in the liner being injected into the GC column. Examples of packing material include glass wool, which represents the dominant packing material employed in modern liners, and porous carbon material.

Glass wool packing material has an entangled configuration of glass wool fibers, making it a suitable material to help promote sample vaporization and to trap non-volatile residue which may be present in "dirty" samples. However, the silanol surface of glass wool is prone to substantial adsorption of organic compounds and has been demonstrated to promote chemical breakdown of many analytes. Further, glass wool is a thermal insulator and therefore is not an ideal material for promoting efficient thermal transfer to the liquid sample mixture to be analyzed. In an effort to overcome surface reactivity and adsorption, glass wool is chemically deactivated. However, the process used to chemically deactivate the glass wool is never really complete, and exposed silanol domains on the glass wool remain after the deactivation process. Further, as the glass wool is handled, its fibers tend to break, thereby exposing new active sites. Also, glass wool packing material is difficult to pack into small diameter and medium diameter inlet liners.

Porous carbon materials, such as CarboFrit packing material, have been described as suitable materials for liner packing. However, commercially available examples of CarboFrit packed liners indicate that CarboFrit packing material is very delicate, having an increased risk of particle fine production when handled. Although there may be a marginal improvement in performance using CarboFrit packed liners rather than glass wool packed liners, the marginal improvement may be seen by some as not justifying the increased cost involved in using CarboFrit packed liners rather than glass wool packed liners.

It would be desirable to have an inlet liner insert (e.g., packing) that promotes sample vapor mixing without completely occluding the vapor path through an inlet liner, that has a surface that is inert and causes little or no breakdown or chemical modification of the sample being tested, that does not permanently adsorb components of the sample being analyzed, that promotes quick temperature transfer (e.g., has a high thermal conductivity) to insure efficient volatilization of the liquid sample to be tested, and that has a high surface area to volume ratio.

SUMMARY OF THE INVENTION

It is an object of the invention to provide a sleeve unit, which comprises an inlet liner and an inlet liner insert positioned therein, for preparing a sample for gas chromatographic analysis, as well as the inlet liner insert itself, wherein the surface of the inlet liner insert is inert or substantially inert to the sample being tested.

It is an object of the invention to provide a sleeve unit, which comprises an inlet liner and an inlet liner insert positioned therein, for preparing a sample for gas chromatographic analysis, as well as the inlet liner insert itself, wherein the surface of the inlet liner insert has a high thermal conductivity. It is an object of the invention to provide a sleeve unit, which comprises an inlet liner and an inlet liner insert positioned therein, for preparing a sample for gas chromatographic analysis, as well as the inlet liner insert itself, wherein the surface of the inlet liner insert has a high surface area to volume ratio.

It is an object of the invention to provide a sleeve unit, which comprises an inlet liner and an inlet liner insert positioned therein, for preparing a sample for gas chromatographic analysis, as well as the inlet liner insert itself, wherein the surface of the inlet liner insert has a high resistance to sample adsorption, especially over about 150° C.

These and other objects are accomplished by our invention, which is set out below.

BRIEF DESCRIPTION OF THE DRAWINGS

FIG. 1b is a top plan view of the inlet sleeve of FIG. 1a.

FIG. 2b is a top plan view of the inlet sleeve of FIG. 2a.

FIG. 3b is a top plan view of the inlet sleeve of FIG. 3a.

FIG. 4b is a top plan view of the inlet sleeve of FIG. 4a.

FIG. 5b is a top plan view of the inlet sleeve of FIG. 5a.

DETAILED DESCRIPTION

Figure 1A:
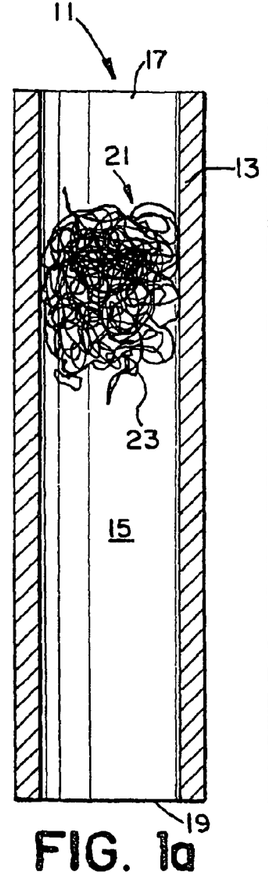
FIG. 1a is a view of an inlet sleeve constructed in accordance with the invention, in which the inlet liner is shown in cross-section and the inlet liner insert positioned in the inlet liner is shown in front elevation.
Figure 1B:
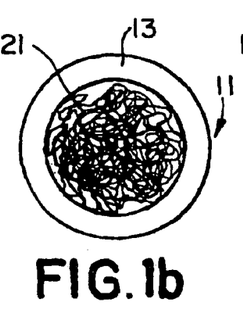

Turning now to the drawings, there are shown a plurality of preferred embodiments of our invention. Turning first to FIGS. 1(a) and 1(b), there is shown a sleeve unit 11 for preparing a sample for gas chromatographic analysis. The sleeve unit 11 has an inlet liner 13 that has a bore 15 therein, an inlet 17 to the bore 15, and an outlet 19 from the bore 15. An inlet liner insert (packing) 21 is located within the bore 15.

Preferably, the inlet liner 13 is made of glass, and generally may be any type of inlet liner that may be used with packing, such as straight and gooseneck splitless liners, straight split injection liners, open top Uniliner direct injection liners, and drilled Uniliner liners.

The inlet liner insert 21, when positioned inside an inlet liner 13, extends across the bore 15 of the inlet liner 13 to cause the sample being prepared for gas chromatographic analysis to flow through the inlet liner inert 21. The inlet liner insert 21 comprises an arrangement of wire 23, which creates a restricted pathway for the sample being prepared for gas chromatographic analysis as the sample moves through the bore 15 of the inlet liner 13 to the outlet 19 of the bore 15. Preferably, the inlet liner insert 21 is sized that portions of it press tightly against the wall of the inlet liner 13 that defines the bore 15 to fix the inlet liner insert 21 in place in the inlet liner 13. However, the inlet liner insert 21 of the invention also may be sized such that when it is positioned within an inlet liner 13 it is not fixed in place in the inlet liner 13.

The wire 23 has a surface having a high thermal conductivity and is substantially chemically inert to the sample being prepared for gas chromatographic analysis. The wire 23 has an inert metal surface, and preferably comprises wire coated with an inert metal or wire consisting essentially of an inert metal. Preferably, the inert metal comprises gold or platinum.

Preferably, the inlet liner insert 21 comprises a single wire 23 having two ends. However, the inlet liner insert 21 may comprise more than one wire 23. The wire 23 preferably has a diameter between about 0.0001 inches (about 2.5 microns) and about 0.002 inches (about 50 microns), which is approximately the same diameter of glass wool fibers found in commercial glass wool packing. Even more preferred is wire 23 having a diameter between about 0.0002 inches (about 5 microns) and about 0.001 inches (about 25 microns). Particularly preferred is wire 23 having a diameter of about 0.0005 inches (about 12.5 microns). Thin diameter gold wire is commercially available with chemical purities on the order of 99.995%. In particular, thin diameter, high purity gold wire, such as that sold by Semiconductor Packaging Materials, of Armonk, N.Y., is commonly employed in the semiconductor industries for electrical connection between integrated chips and substrates.

FIGS. 1a and 1b illustrate a preferred embodiment in which the inlet liner insert 21 has an entangled wire configuration. This configuration simulates the configuration of glass wool packing. In contrast to glass wool packing which has many fibers, the wire 23 may be limited, if desired, to be a single wire having only two ends.

The inlet liner insert 21 may be made by hand or using tweezers to bend the wire 23 at various points along its length to form the entangled wire configuration illustrated in FIGS. 1a and 1b, and the inlet liner insert 21 may be positioned in the inlet liner 13 by inserting the inlet liner insert 21 through the inlet 17 into the bore 15 and, if necessary, using a rod or the like to push the inlet liner insert 21 into the desired position in the inlet liner 13.

FIGS. 2a-2b, 3a-3b, 4a-4b, 5a-5b, and 6a-6b illustrate other preferred embodiments of the invention. In these preferred embodiments, the inlet liner inserts 121, 221, 321, 421, and 521, like inlet liner insert 21, are an arrangement of inert metal wire 23. However, rather than having the entangled wire configuration of inlet liner insert 21, the inlet liner inserts of these embodiments have different shapes/configurations.

Figure 2A:
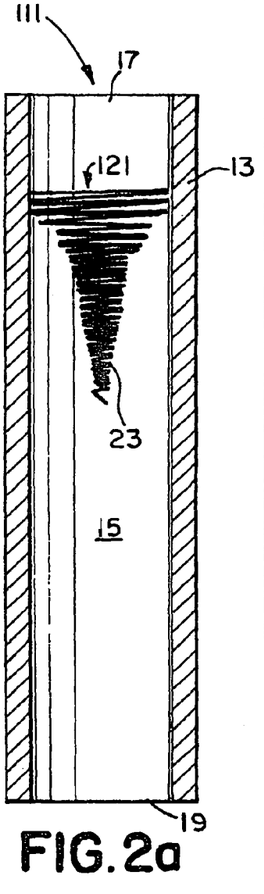
FIG. 2a is a view of an inlet sleeve constructed in accordance with the invention, in which the inlet liner is shown in cross-section and the inlet liner insert positioned in the inlet liner is shown in front elevation.
Figure 2B:
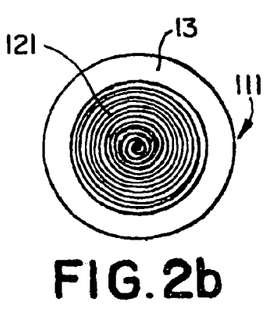

FIGS. 2a and 2b illustrate an inventive sleeve unit 111 which is identical to the sleeve unit 11, except inlet liner insert 21 is replaced with an inlet liner insert 121 which has a tornado-like shape. The configuration of this preferred embodiment draws the liquid sample being prepared for chromatographic analysis to the center of the inlet liner 13, thereby reducing wall effects. Further, the configuration of this preferred embodiment minimizes the amount of contact between the inlet liner insert (the packing) 121 and the inlet liner 13. The inlet liner insert 121 may be made by winding wire 23 around a cone-shaped form, preferably starting at the base of the cone-shaped form and winding the wire 23 around the cone-shaped form until the apex of the cone-shaped form is reached, and then either pulling the inlet liner insert 121 that is formed on the cone-shaped form off the cone-shaped form or pulling the cone-shaped form from the inlet liner insert 121 created by such winding of the wire 23 around the cone-shaped form.

Figure 3A:
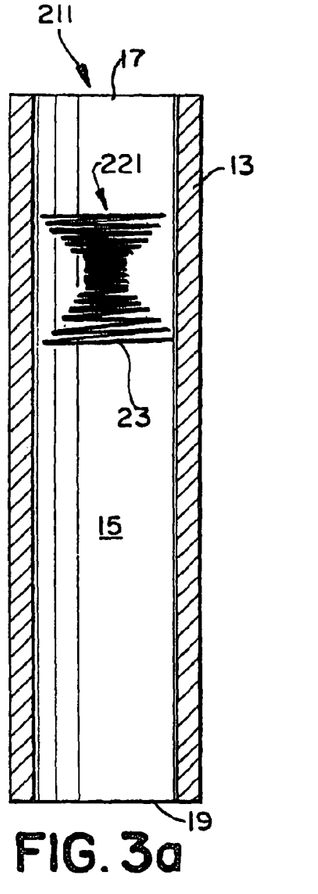
FIG. 3a is a view of an inlet sleeve constructed in accordance with the invention, in which the inlet liner is shown in cross-section and the inlet liner insert positioned in the inlet liner is shown in front elevation.
Figure 3B:
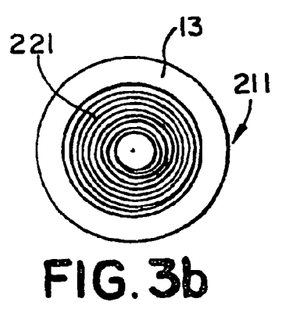
Figure 7:
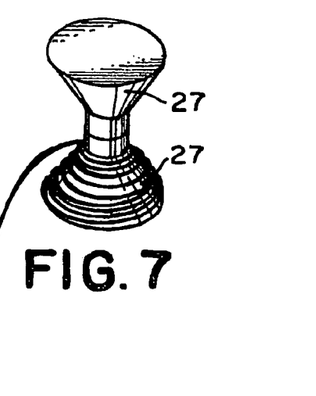
FIG. 7 is a view in perspective showing wire 23 being wound around two forms 27 to form an inlet liner insert 221.

FIGS. 3a-3b illustrate an inventive sleeve unit 211 which is identical to sleeve unit 11, except inlet liner insert 21 is replaced with an inlet liner insert 221 which has a spring or hour glass shape/configuration. The configuration of this preferred embodiment draws the liquid sample being prepared for chromatographic analysis to the center of the inlet liner 13, thereby reducing wall effects. Further, the configuration of this preferred embodiment minimizes the amount of contact between the inlet liner insert (the packing) 221 and the inlet liner 13. Inlet liner insert 221 may be formed by winding a wire 23 around two substantially cone-shaped forms 27 that have a cylindrical portion formed at the apex of the form. The two forms 27 may be held together such that the cylindrical shaped apex of one of the forms 27 abuts against the cylindrical shaped apex portion of the other form 27, and wire 23 may be wound around the forms 27 as they are held together, preferably starting at the base of the first form 27 and winding the wire 23 around the forms 27 until the base of the second form 27 is reached, as illustrated FIG. 7. Upon completion of the winding of the wire 23 around the forms 27, the forms 27 may be separated from the ends of the formed inlet liner insert 221.

Figure 4A:
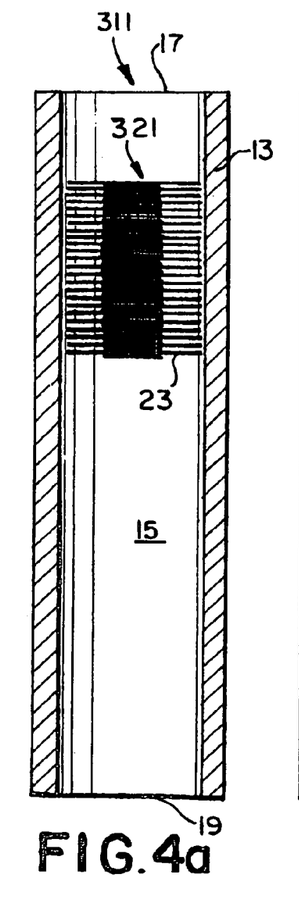
FIG. 4a is a view of an inlet sleeve constructed in accordance with the invention, in which the inlet liner is shown in cross-section and the inlet liner insert positioned in the inlet liner is shown in front elevation.
Figure 4B:
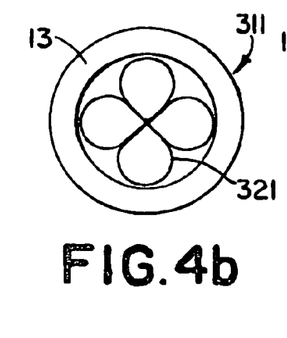
Figure 8:
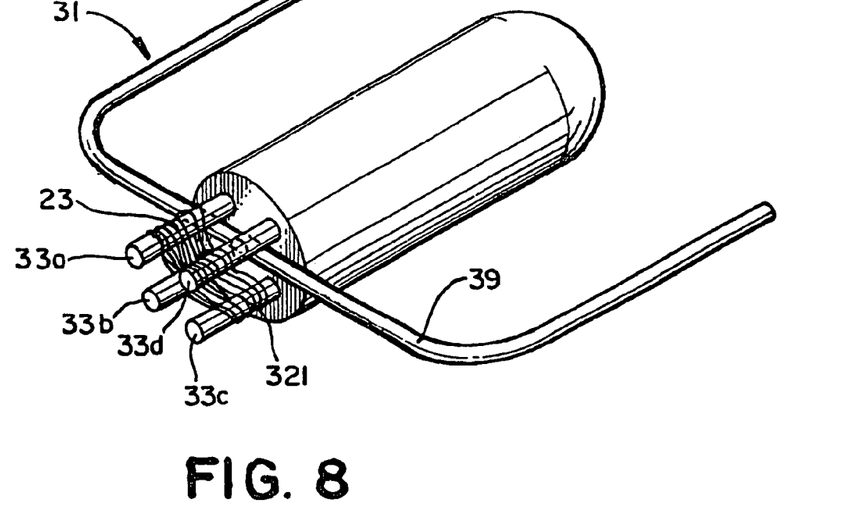
FIG. 8 is a view in perspective showing a device 31 which may be used to form woven inlet liner inserts of the invention.
Figure 9:
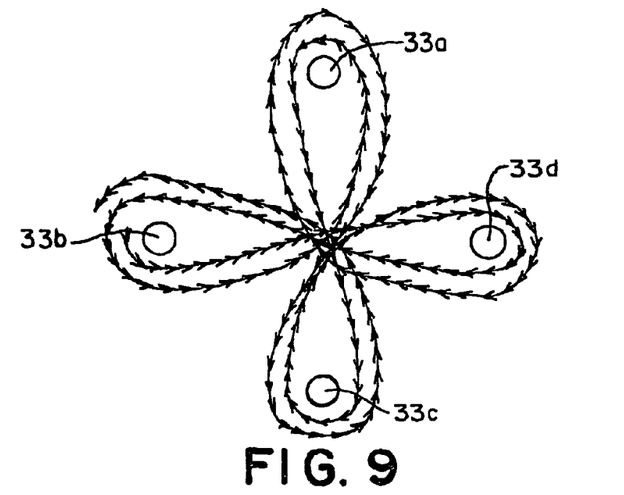
FIG. 9 illustrates a weaving pattern that may be followed to weave wire 23 around posts 33a-33d to obtain the weave pattern shown in FIGS. 4a-4b for inlet liner insert 321.

FIGS. 4a-4b illustrate an inventive sleeve unit 311 which is identical to the sleeve unit 11, except inlet liner insert 21 is replaced with an inlet liner insert 321 which has a weave pattern configuration. The inlet liner insert 321 may be made by weaving wire 23 around a series of posts to form an inlet liner insert 321 having the weave pattern desired to be used. The number of posts and the weave pattern chosen may be varied as desired (e.g., 3, 4, 5, or other number of posts—the limiting factor on the number of posts that may be used being the inner diameter of the inlet liner 13). For example, FIG. 8 shows a device 31 used to form an inlet liner insert 321. Device 31 has four posts 33a, 33b, 33c, and 33d around which wire 23 may be woven to form the inlet liner insert 321 having the weave pattern shown in FIGS. 4a-4b. To obtain this weave pattern, wire 23 may be woven around the posts 33a, 33b, 33c, and 33d following the arrows shown in FIG. 9. Upon completion of the weaving, the inlet liner insert 321 formed on the device 31 may be removed from the device 31 by sliding it off the posts 33a-33d.

Figure 10A:
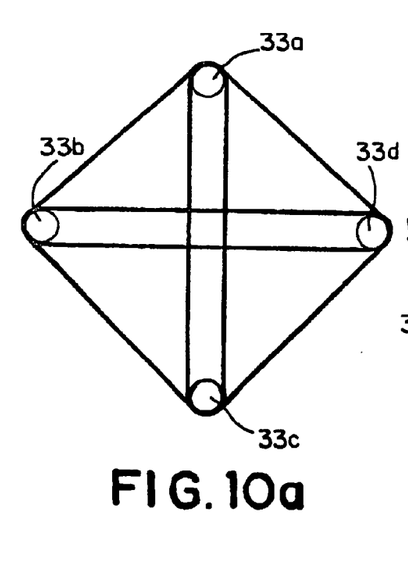
FIG. 10a illustrates another preferred weave pattern.
Figure 10B:
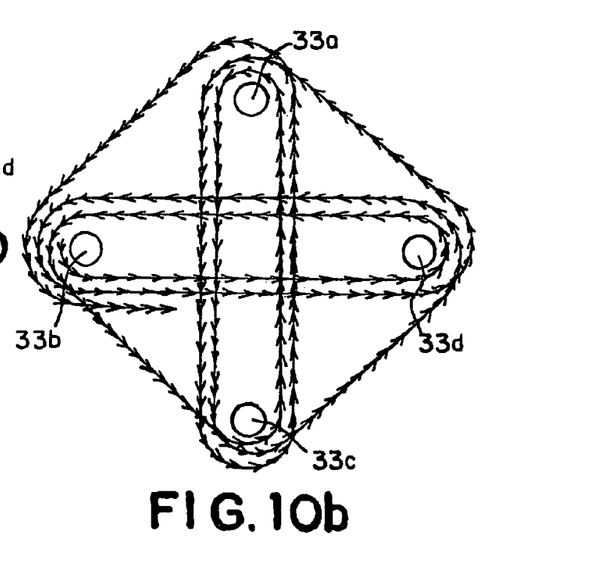
FIG. 10b illustrates a weaving pattern that may be followed to weave wire 23 around posts 33a-33d to obtain the weave pattern shown in FIG. 10a for the inlet liner insert 321.
Figure 11A:
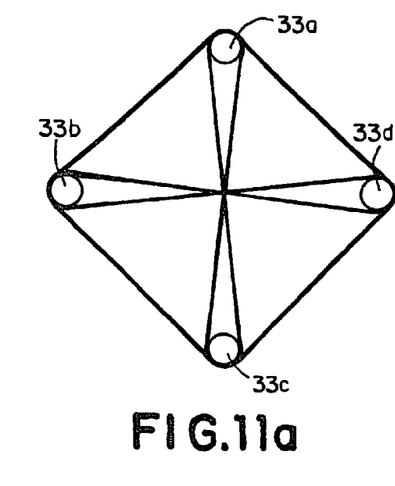
FIG. 11a illustrates another preferred weave pattern.
Figure 11B:
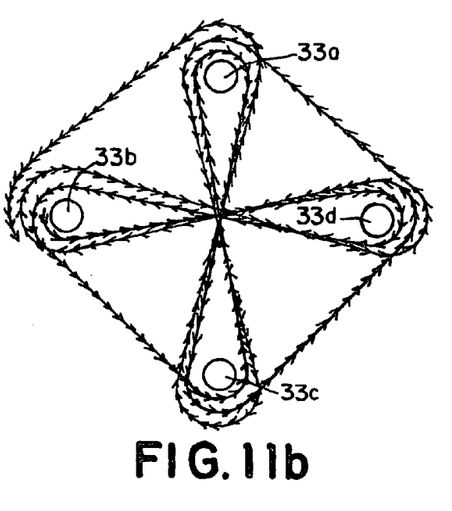
FIG. 11b illustrates a weaving pattern that may be followed to weave wire 23 around posts 33a-33d to obtain the weave pattern shown in FIG. 11a for the inlet liner insert 321.
Figure 12A:
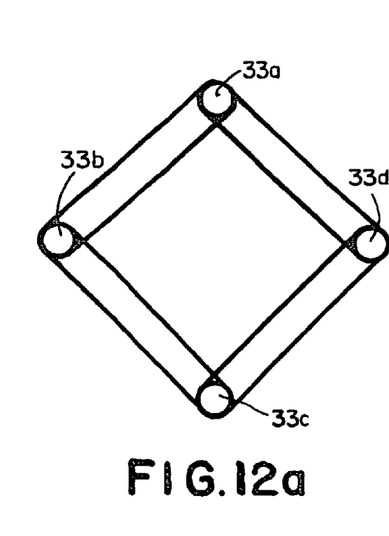
FIG. 12a illustrates another preferred weave pattern.
Figure 12B:
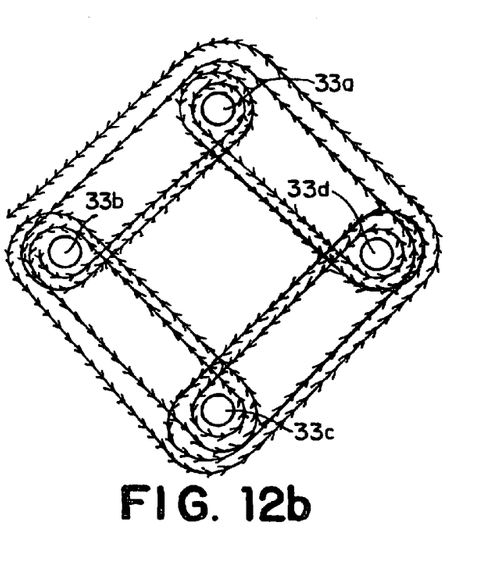
FIG. 12b illustrates a weaving pattern that may be followed to weave wire 23 around posts 33a-33d to obtain the weave pattern shown in FIG. 12a for the inlet liner insert 321.

FIGS. 10a, 11a, and 12a illustrate other preferred weave patterns that may be woven on device 31. Any of the weave patterns shown in FIGS. 4a, 4b, 10a, 11a, and 12a, or a combination of these weave patterns, may be used for the inventive inlet liner insert 321. To obtain the weave patterns shown in FIGS. 10a, 11a, and 12a, wire 23 may be woven around the posts 33a, 33b, 33c, and 33d following the arrows shown in FIG. 10b to obtain the weave pattern of FIG. 10a, the arrows shown in FIG. 11b to obtain the weave pattern of FIG. 11a, and the arrows shown in FIG. 12b to obtain the weave pattern of FIG. 12a. Again, the completed woven inlet liner insert 321 may be slid off the posts 33a-33d for use in an inlet liner 13.

To assist in removing a woven inlet liner insert 321 from the device 31, a cross bar 39, illustrated in FIG. 8, preferably is provided, and may be used to push the woven inlet liner insert 321 off the device 31. The cross bar 39 is placed between a number of posts of the device 31 at the base of the posts and is moved to the free ends of the posts to push the woven inlet liner insert 321 which has been woven on the device 31 off the device 31.

Figure 13:
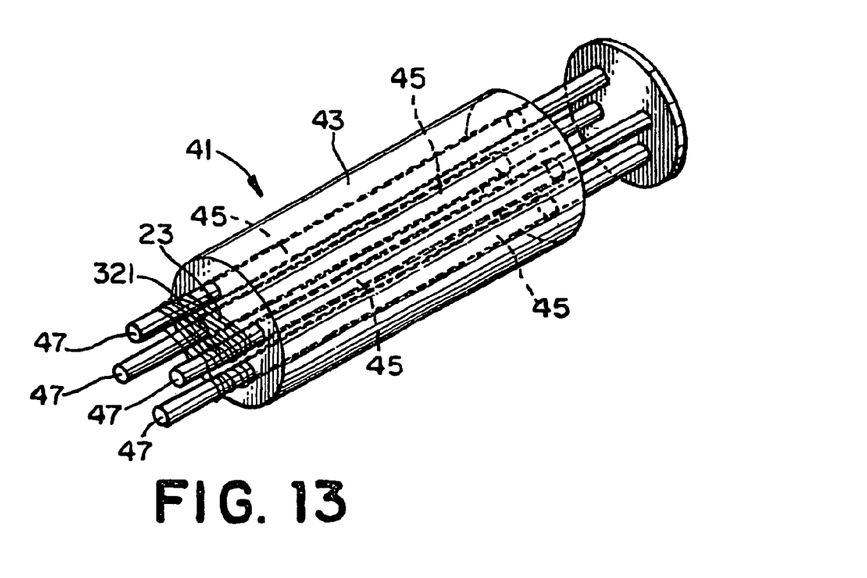
FIG. 13 is a view in perspective showing a device 41 which may be used to form woven inlet liner inserts of the invention.
Figure 14:
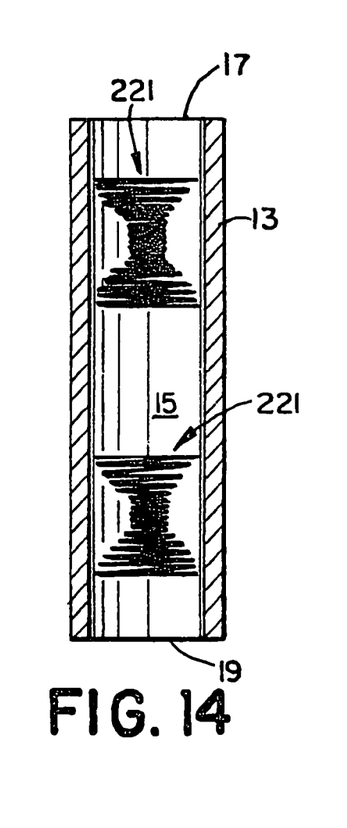
FIG. 14 is a view of another preferred sleeve unit of the invention, in which the inlet liner is shown in cross-section and the two inlet liner inserts positioned therein are shown in front elevation.

Alternatively, a device 41, illustrated in FIG. 13, may be used to form a woven inlet liner insert 321 of the invention. Here, device 41 has a body 43 having four bores 45 sized to receive posts 47 that are joined together at one end. The free ends of the posts 47 may be slid through the bores 45 such that they protrude from the body 43 to receive wire 23 woven thereon to form a woven inlet liner insert 321. After the woven inlet liner insert 321 is woven from wire 23 onto the free ends of the posts 47, the woven inlet liner insert 321 may be removed from the posts 47 by withdrawing the posts 47 from the body 43. Preferably, after a woven inlet liner insert 321 of the invention has been woven on device 41, the woven inlet liner insert 321 is positioned in the inlet liner 13 by inserting the posts 47 of device 41 into the inlet liner 13 before the inlet liner insert 321 is removed from the device 41, and then withdrawing the posts 47 from the body 43 and thereby leaving the inlet liner insert 321 in the inlet liner 13. If necessary, a rod may be inserted into the inlet liner 13 to re-position the woven inlet liner insert 321 which has been placed in the inlet liner 13 using the device 41.

Other weave patterns may be obtained for the inlet liner insert 321 by weaving wire 23 in other patterns using the four posts of devices 31 or 41, or by weaving wire 23 in any desired pattern around a series of posts, other than four posts, such as three posts, five posts, or any other number of posts.

Figure 5A:
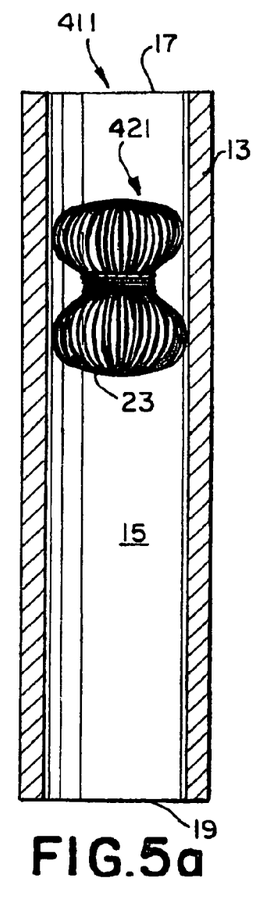
FIG. 5a is a view of an inlet sleeve constructed in accordance with the invention, in which the inlet liner is shown in cross-section and the inlet liner insert positioned in the inlet liner is shown in front elevation.
Figure 5B:
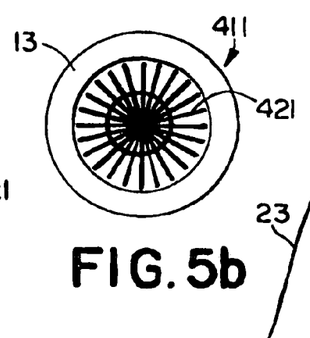

FIGS. 5a-5b illustrate an inventive sleeve unit 411 which is identical to the sleeve unit 11, except inlet liner insert 21 is replaced with an inlet liner insert 421 which has a rounded hour glass shape/configuration with the wire 23 in the side portions of its upper and lower halves extending with respect to the view shown in FIG. 5a in an up and down direction, as opposed to a side to side direction. The inlet liner insert 421 may be made by winding the wire 23" around a rod, sliding the wound wire 23 from the rod and bunching it along what was the axial center line when the wire 23 was on the rod to form an upper end portion and a lower end portion, and then winding an end portion of the wire 23 around the middle bunched area. The upper end and lower end portions are then fanned apart to form a configuration that is like the head of a whisk used to mix things when cooking. Manufactured products employing pure gold or platinum are of course cost sensitive, and this configuration has the advantage of creating a comparatively large packing using only a small amount of gold or platinum wire 23.

Figure 6:
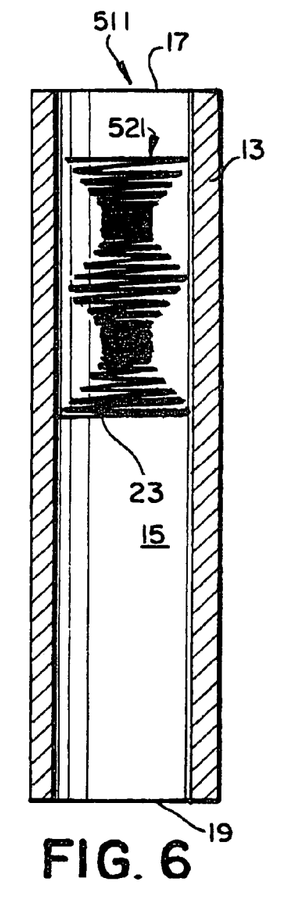
FIG. 6 is a view of an inlet sleeve constructed in accordance with the invention, in which the inlet liner is shown in cross-section and the inlet liner insert positioned in the inlet liner is shown in front elevation.

FIG. 6 illustrates an inventive sleeve unit 511 which is identical to the sleeve unit 11, except inlet liner insert 21 is replaced with an inlet liner insert 521 which has a shape of a second hour glass stacked upon a first hour glass, such as if the inlet liner insert 221 were stacked upon itself. Inlet liner insert 521 may be formed in a similar fashion to inlet liner insert 221 by winding wire 23 around two substantially cone-shaped forms 27 (see FIG. 7) that have a cylindrical portion formed at the apex of each form 27. The two forms 27 may be held together such that the cylindrical shaped apex of one of the forms 27 abuts against the cylindrical shaped apex portion of the other form 27, and wire 23 may be wound around the forms 27, preferably starting at the base of the first form 27 and winding the wire 23 around the forms 27 until the base of the second form 27 is reached, as illustrated FIG. 7. Upon completion of the winding of the wire 23 around the forms 27, the forms 27 may be removed from the ends of the partially formed inlet liner insert 521 of this embodiment. Then, the forms 27 may again be held together, again apex to apex, and positioned such that the base of one of the forms 27 is positioned at the end of the partially formed inlet liner insert 521 where winding left off. Winding of the wire 23 then is continued by winding the wire 23 around the abutting forms 27 until the base of the second form 27 is reached, thereby forming the inlet liner insert 521 having the shape of a second hour glass stacked on a first hour glass. The form 27 at the open end of the inlet liner insert 521 may be pulled from the open end of the inlet liner insert 521, and the other form 27 may be removed from inside the inlet liner insert 521 by temporarily bending the inlet liner insert 521 open at its middle portion to permit the form 27 to be removed, and then the middle portion of the inlet liner insert 521 may be bent back so that inlet liner insert 521 regains its shape of an hour glass stacked on an hour glass.

Unlike glass wool, which is composed of multiple individual interlocking fibers, the inert metal wire 23 (such as gold wire 23, gold coated wire 23, platinum wire 23, or platinum coated wire 23) of the invention is contiguous. It is therefore possible to control the size, shape, configuration, and total amount of inert metal in the wire packing insert 21, 121, 221, 321, 421, and 521. Premeasured contiguous lengths of wire 23 may be used to insure uniform amounts of wire 23 in each inlet liner insert, which leads to the formation of uniform inlet liner inserts, and uniform inlet liner inserts lead to uniformity of gas chromatographic analysis results. Manufactured products employing pure gold or platinum are of course cost sensitive, and the use of wire 23 to form the inventive inlet liner inserts permits the creation of a comparatively large packing using only a small amount of gold or platinum.

Figure 15:
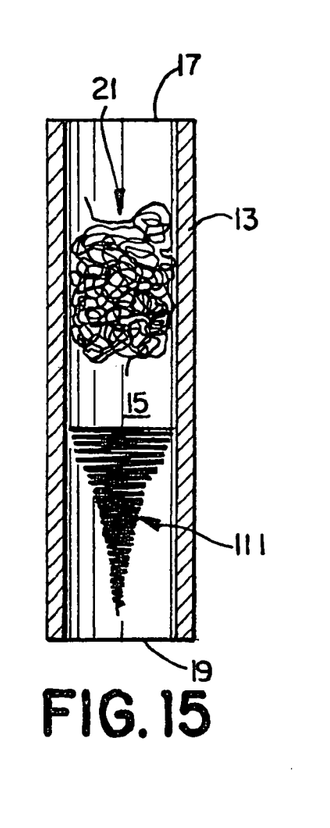
FIG. 15 is a view of another preferred sleeve unit of the invention, in which the inlet liner is shown in cross-section and the two inlet liner inserts positioned therein are shown in front elevation.
Figure 16:
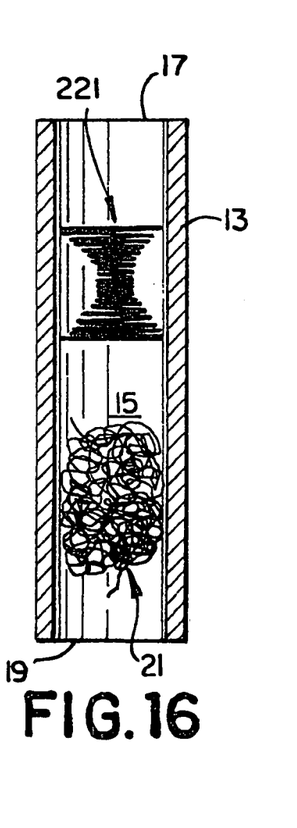
FIG. 16 is a view of another preferred sleeve unit of the invention, in which the inlet liner is shown in cross-section and the two inlet liner inserts positioned therein are shown in front elevation.
Figure 17:
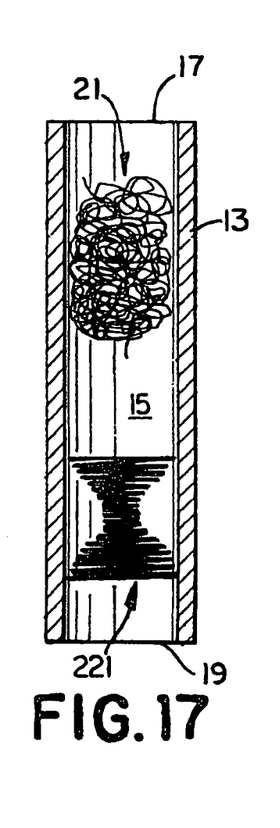
FIG. 17 is a view of another preferred sleeve unit of the invention, in which the inlet liner is shown in cross-section and the two inlet liner inserts positioned therein are shown in front elevation.

FIGS. 14, 15, 16, and 17 show additional alternative embodiments of the invention, in which the inlet liner 13 is provided with a plurality of inlet liner inserts. In these illustrative FIGS. 14, 15, 16 and 17, the inlet liner 13 is provided with two inlet liner inserts. However, if desired, more than two inlet liner inserts may be provided in the inlet liner 13. Also, when a plurality of inlet liner inserts are positioned in inlet liner 13, the inlet liner inserts may all have the same configuration, such as that illustrated in FIG. 14 (which shows two inlet liner inserts 221 in inlet liner 13 for illustrative purposes), or the inlet liner inserts may comprise a combination of inlet liner inserts having different configurations, such as is illustrated in FIG. 15, where an inlet liner insert 21 is positioned in an inlet liner 13 in combination with an inlet liner insert 111, or such as is illustrated FIG. 16, where an inlet liner insert 221 is positioned in the inlet liner 13 in combination with an inlet liner insert 21, or such as is illustrated in FIG. 17, where an inlet liner insert 21 is positioned in combination with an inlet liner insert 221. Also, when a plurality of inlet liner inserts is used in an inlet liner 13, the order of where they are located in the inlet liner 13 may be varied as desired. For instance, FIG. 16 shows inlet liner insert 221 positioned above the inlet liner insert 21 in inlet liner 13. However, this order may be rearranged such that the inlet liner insert 21 is located above inlet liner insert 221, if desired, as shown in FIG. 17.

Each of the inlet liner inserts of the invention may be positioned in a inlet liner 13 to form an inventive sleeve unit 11, 111, 211, 311, 411, 511, and this may be accomplished by inserting an inlet liner insert of the invention through the inlet 17 into the bore 15 of an inlet liner 13, and, if necessary, using a rod or the like to push the inlet liner insert into the desired position in the liner 13.

In use, an inventive sleeve unit, having one or more of the inventive inlet liner inserts positioned in its inlet liner 13, is positioned in a gas chromatograph. A sample to be analyzed is prepared for gas chromatographic analysis by being introduced to the inlet liner 13 through the inlet 17 to the bore 15 of the inlet liner 13. The inlet liner 13, and the sample contain therein, is subjected to heating (to elevated temperatures, e.g., over 150° C.) to vaporize the sample to be analyzed, and the sample is passed through the inlet liner 13 and the inventive inlet liner insert(s) contained therein forming a volatized substantially homogenous sample gas that my pass through the outlet 19 of the bore 15 to be subjected to gas chromatographic analysis.

Tests were conducted to determine the effectiveness of the inventive inlet sleeve and the inventive inlet liner insert by conducting chromatographic analysis of known samples and comparing the resulting chromatographic analysis profiles of the tested samples with established known profiles for such compositions. The chromatographic analysis profiles obtained for the samples tested closely matched the established known profiles for such compositions.

In particular, tests were conducted using the following instrumentation on organochlorine pesticide mix AB #2 (Restek part number 32292) (some components of which are known to be reactive and thermally unstable) under the following run conditions:

Instrument
Agilent 6890 GC,
Agilent split-splitless injection port,
Restek 2 mm splitless liner 13 for Agilent GCs (Restek part number 20712), with a preferred inventive gold wire inlet liner insert 321 shown in FIGS. 4a and 4b added thereto (the inlet wire insert 321 being formed from gold wire 23 having a length of 24 inches, a diameter of about 0.0005 inches, and a 99.995% purity),
Restek GC column; Rxi®-1 ms 30-Meter; 0.25 mm ID; 0.25 µm df (Restek part number 13323)
Agilent micro-ECD detector (an electron capture detector), nitrogen makeup gas
Run Conditions
GC oven maximum temperature: 350° C.
Inlet temperature: between 100° C. and 350° C.
Helium carrier gas
Splitless injection mode
Inlet purge time, 60 sec.
Inlet purge flow, 40 mL/min.
Inlet total flow, 41.3 mL/min.
Septum purge flow, 3 mL/min.
Makeup gas flow+column flow, 50 mL/min.
Oven temperature:
Initial, 100° C.
1 minute hold,
Ramp 100° C.-300° C.@10° C./min.

The chromatographic analysis profiles obtained for the organochlorine pesticide mix AB #2 samples that were tested closely matched the established profile known for organochlorine pesticide mix AB #2. The results of these tests also showed that use of the inventive inlet sleeve and the inventive inlet liner insert permitted a wider temperature range to be used without detrimental effects to the chromatographic analysis of the samples tested.

Comparison of Properties of Prior Art versus Properties of the Invention

The following table sets out a comparison of the properties of the prior art versus the properties of the invention.

TABLE 1

| Property | Glass wool, untreated | Glass wool, deactivated | Carbofrit | Inventive Inlet Liner Insert |
|---|---|---|---|---|
| inertness | low | moderate | high | high |
| thermal conductivity | low | low | moderate | high |
| surface area/volume | high | high | moderate | high |
| resistance to sample adsorption (e.g., over about 150° C.) | low | moderate | moderate | high |

Although untreated glass wool packing has an excellent surface to volume ratio, which promotes the formation of a substantially homogenous sample gas, it suffers from drawbacks such of being prone to substantial adsorption of organic compounds and promotion of chemical breakdown of many analytes due to having a low resistance to sample adsorption and to not being inert. Further, since untreated glass wool has, a low thermal conductivity, it is not ideal for promoting efficient thermal transfer to the liquid sample mixture to be analyzed.

Although deactivated glass wool packing has an excellent surface area to volume ratio, which promotes the formation of a substantially homogenous gas sample, and has better properties than untreated glass wool packing with respect to surface reactivity and adsorption, the exposed silanol domains on the glass wool remain after the deactivation process, and new active sites are created on the glass wool packing as fibers break. The deactivated glass wool packing also suffers from the drawback for having a low thermal conductivity which hinders efficient thermal transfer to the liquid sample mixture to be analyzed.

While the CarboFrit packing is highly inert and therefore resistant to chemical breakdown of analytes, the CarboFrit packing material is only moderately resistant to sample adsorption, only has a moderate surface area to volume ratio (which adversely affects promotion of vaporization and mixing of sample), and only has moderate thermal conductivity properties (which adversely affects promotion of efficient thermal transfer to the liquid sample mixture).

In contrast to the untreated glass wool packing, the deactivated glass wool packing, and the CarboFrit packing, the inlet liner insert of the invention has high marks for all of the properties listed in TABLE 1. Because the inventive inlet liner insert is highly inert, it guards against chemical breakdown of many analytes. Further, because the inventive inlet liner insert has a high surface area to volume ratio, it promotes vaporization of the liquid sample and mixing to form a substantially homogenous gas sample to be analyzed. The inventive inlet liner insert has a high resistance to sample adsorption, and a high thermal conductivity which promotes efficient thermal transfer to the liquid sample mixture which is to be vaporized prior to being analyzed.

Due to the configurations of the inventive inlet liner inserts, non-volatile residue, such as solid/high molecular weight contaminants, which may be present in "dirty" samples, may be trapped in the inlet liner 13 by the inlet liner insert of the invention to prevent column contamination. Further, the inventive inlet liner inserts promote sample vapor mixing to obtain homogenous samples, and assist in reaching ideal vapor residence time in the inlet liner prior to the vapor sample formed in the inlet liner being injected into the GC column. The inventive inlet liner inserts promote efficient sample volatization and efficient sample vapor mixing to ensure formation of substantially homogenous samples that may comprise of volatile components.

What is claimed:

1. A sleeve unit for preparing a sample for gas chromatographic analysis, comprising:
   an inlet liner having a bore therein, an inlet to the bore, and an outlet from the bore, and
   an inlet liner insert located within the bore,
   the inlet liner insert extending across the bore to cause a sample being prepared for gas chromatographic analysis to flow through the inlet liner insert,
   the inlet liner insert comprising an arrangement of wire,
   the arrangement of wire creating a restricted pathway for the sample as the sample flows through the bore of the inlet liner to the outlet of the bore, and
   the wire having a surface having a high thermal conductivity and being substantially chemically inert to the sample.

2. The sleeve unit of claim 1, the wire consisting essentially of gold.

3. The sleeve unit of claim 1, the wire being gold wire.

4. The sleeve unit of claim 1, the wire being gold coated wire.

5. The sleeve unit of claim 1, the wire consisting essentially of platinum.

6. The sleeve unit of claim 1, the wire being platinum wire.

7. The sleeve unit of claim 1, the wire being platinum coated wire.

8. The sleeve unit of claim 1, the wire having a diameter between about 0.0001 inches and about 0.002 inches.

9. The sleeve unit of claim 1, the wire having a diameter of about 0.0002 inches and about 0.001 inches.

10. The sleeve unit of claim 1, the wire having a diameter between about 0.0005 inches.

11. The sleeve unit of claim 1, the inlet liner insert being a single wire having two ends.

12. The sleeve unit of claim 1, the inlet liner being packed with more than one inlet liner insert.

13. The sleeve unit of claim 1, the arrangement of wire having a configuration that directs the sample being prepared for gas chromatographic analysis toward the center of the inlet liner.

14. The sleeve unit of claim 1, the inlet liner insert having an hour glass shape.

15. The sleeve unit of claim 1, the inlet liner insert having a shape of a second hour glass stacked on a first hour glass.

16. The sleeve unit of claim 1, the inlet liner insert having an hour glass shape/configuration having whisk-head like upper and lower end portions.

17. The sleeve unit of claim 1, the inlet liner insert having a tornado-like shape.

18. The sleeve unit of claim 1, the inlet liner insert having a weave pattern configuration.

19. The sleeve unit of claim 1, the inlet liner insert having an entangled wire configuration.

20. The sleeve unit of claim 1, the inlet liner being packed with at least two inlet liner inserts, with at least two of the inlet liner inserts having different configurations.

21. The sleeve unit of claim 1,
   the wire being gold wire,
   the wire having a diameter between about 0.0005 inches and about 0.002 inches,
   the inlet liner insert being a single wire having two ends, and
   the inlet liner insert having an entangled wire configuration.

22. The sleeve unit of claim 1,
   the wire consisting essentially of platinum or the wire being platinum coated,
   the wire having a diameter between about 0.0005 inches and about 0.002 inches,
   the inlet liner insert being a single wire having two ends, and
   the inlet liner insert having an hour glass shape, a shape of a second hour glass stacked on a first hour glass, an hour glass shape/configuration having whisk-head like upper and lower end portions, a tornado-like shape, a weave pattern configuration, or an entangled wire configuration.

23. An inlet liner insert for an inlet liner used in preparing a sample for gas chromatographic analysis, the inlet liner having a bore therein, an inlet to the bore, and an outlet from the bore, comprising:
  an arrangement of wire,
  the inlet liner insert being sized to extend across the bore of the inlet liner to cause a sample being prepared for gas chromatographic analysis in the inlet liner to flow through the inlet liner insert,
  the arrangement of wire creating a restricted pathway for the sample as the sample flows along the bore of the inlet liner to the outlet of the bore, and
  the wire having a surface having a high thermal conductivity and being substantially chemically inert to the sample.

24. The inlet liner insert of claim 23, the wire consisting essentially of gold.

25. The inlet liner insert of claim 23, the wire being gold wire.

26. The inlet liner insert of claim 23, the wire being gold coated wire.

27. The inlet liner insert of claim 23, the wire consisting essentially of platinum.

28. The inlet liner insert of claim 23, the wire being platinum wire.

29. The inlet liner insert of claim 23, the wire being platinum coated wire.

30. The inlet liner insert of claim 23, the wire having a diameter between about 0.0001 inches and about 0.002 inches.

31. The inlet liner insert of claim 23, the wire having a diameter between about 0.0002 and about 0.001 inches.

32. The inlet liner insert of claim 23, the wire having a diameter of about 0.0005 inches.

33. The inlet liner insert of claim 23, the inlet liner insert being a single wire having two ends.

34. The inlet liner insert of claim 23, the arrangement of the wire having a configuration that directs the sample being prepared for gas chromatographic analysis toward the center of the inlet liner.

35. The inlet liner insert of claim 23, the inlet liner insert having an hour glass shape.

36. The inlet liner insert of claim 23, the inlet liner insert having a shape of a second hour glass stacked on a first hour glass.

37. The inlet liner insert of claim 23, the inlet liner insert having an hour glass shape-configuration having whisk-head like upper and lower end portion.

38. The inlet liner insert of claim 23, the inlet liner insert having a tornado-like shape.

39. The inlet liner insert of claim 23, the inlet liner insert having a weave pattern configuration.

40. The inlet liner insert of claim 23, the inlet liner insert having an entangled wire configuration.

41. The inlet liner insert of claim 23, the inlet liner being packed with at least two inlet liner inserts, with at least two of the inlet liner inserts having different configurations.

42. The inlet liner insert of claim 23,
  the wire being gold wire,
  the wire having a diameter between about 0.0005 inches and about 0.002 inches,
  the inlet liner insert being a single wire having two ends, and
  the inlet liner insert having an entangled wire configuration.

43. The inlet liner insert of claim 23,
  the wire consisting essentially of platinum or the wire being platinum coated,
  the wire having a diameter between about 0.0005 inches and about 0.002 inches,
  the inlet liner insert being a single wire having two ends, and
  the inlet liner insert having an hour glass shape, a shape of a second hour glass stacked on a first hour glass, an hour glass shape having whisk-head like upper and lower end portions, or a tornado-like shape, a weave pattern configuration, or an entangled wire configuration.

44. A method of preparing a sample for gas chromatographic analysis, comprising the steps of:
  introducing a sample to be analyzed using gas chromatography to an inlet liner having a bore therein, an inlet to the bore, an outlet from the bore, and an inlet liner insert located within the bore, the inlet liner insert comprising an arrangement of wire, the inlet liner insert being sized to extend across the bore of the inlet liner to cause a sample being prepared for gas chromatographic analysis in the inlet liner to flow through the inlet liner insert, the arrangement of wire creating a restricted pathway for the sample as the sample flows through the bore of the inlet liner to the outlet of the bore, and the wire having a surface having a high thermal conductivity and being substantially chemically inert to the sample, and
  heating and passing the sample through the inlet liner forming a volatized, substantially homogenous sample gas.

45. The method of claim 44, the wire consisting essentially of gold.

46. The method of claim 44, the wire being gold wire.

47. The method of claim 44, the wire being gold coated wire.

48. The method of claim 44, the wire consisting essentially of platinum.

49. The method of claim 44, the wire being platinum wire.

50. The method of claim 44, the wire being platinum coated wire.

51. The method of claim 44, the wire having a diameter of between about 0.0001 inches and about 0.002 inches.

52. The method of claim 44, the wire having a diameter of between about 0.0002 inches and about 0.001 inches.

53. The method of claim 44, the wire having a diameter of about 0.0005 inches.

54. The method of claim 44, the inlet liner insert being a single wire having two ends.

55. The method of claim 44, the inlet liner being packed with more than one inlet liner insert.

56. The method of claim 44, the arrangement of wire having a configuration that directs the sample being prepared for gas chromatographic analysis toward the center of the inlet liner.

57. The method of claim 44, the inlet liner insert having an hour glass shape.

58. The method of claim 44, the inlet liner insert having a shape of a second hour glass stacked on a first hour glass.

59. The method of claim 44, the inlet liner insert having an hour glass shape/configuration having whisk-head like upper and lower end portions.

60. The method of claim 44, the inlet liner insert having a tornado-like shape.

61. The method of claim 44, the inlet liner insert having a weave pattern configuration.

62. The method of claim 44, the inlet liner insert having an entangled wire configuration.

63. The method of claim 44, the inlet liner being packed with at least two inlet liner inserts, with at least two of the inlet liner inserts having different configurations.

* * * * *